US00RE40914E

(19) United States
(12) Reissued Patent
Taylor et al.

(10) Patent Number: US RE40,914 E
(45) **Date of Reissued Patent: *Sep. 8, 2009**

(54) ORTHOPAEDIC FIXATION PLATE

(75) Inventors: J. Charles Taylor, Memphis, TN (US); Harold S Taylor, Memphis, TN (US)

(73) Assignee: Smith & Nephew, Inc., Memphis, TN (US)

( * ) Notice: This patent is subject to a terminal disclaimer.

(21) Appl. No.: 09/827,252

(22) Filed: Apr. 5, 2001

Related U.S. Patent Documents

Reissue of:
(64) Patent No.: 5,891,143
Issued: Apr. 6, 1999
Appl. No.: 08/954,003
Filed: Oct. 20, 1997

(51) Int. Cl.
*A61B 17/56* (2006.01)

(52) U.S. Cl. ..... 606/56; 606/53; 606/54
(58) Field of Classification Search ..... 606/52, 606/53, 54–61
See application file for complete search history.

(56) References Cited

U.S. PATENT DOCUMENTS

| | | | |
|---|---|---|---|
| 1,308,799 | A | 7/1919 | Masland |
| 2,055,024 | A | 9/1936 | Bittner, Jr. |
| 2,250,417 | A | 7/1941 | Ettinger |
| 2,391,537 | A | 12/1945 | Anderson |

(Continued)

FOREIGN PATENT DOCUMENTS

| | | |
|---|---|---|
| DE | 25 46 046 | 4/1977 |
| DE | 295 03 147.6 | 6/1995 |
| DE | 295 14411 1 U | 1/1996 |
| EP | 0 589 565 | 3/1994 |
| FR | 2 576 774 | 8/1986 |
| FR | 2 756 025 | 11/1996 |
| GB | 108119 | 7/1917 |
| GB | 2 077 847 | 12/1981 |
| SU | 820813 | 4/1981 |
| SU | 1 255 118 | 9/1986 |
| SU | 1 519 673 | 11/1989 |
| WO | WO 91/06253 | 5/1991 |
| WO | WO 92/17313 | 10/1992 |
| WO | WO 96/26678 | 9/1996 |

OTHER PUBLICATIONS

"Monticelli Spinelli External Fixation Systems," pp. 1–28, Pfizer Hospital Products Group, 1991.*

A.S.A.M.I. Group, "Operative Principles of Ilizarov—Fracture Treatment, Nonunion Osteomyelitis, Lengthening Deforimity Correction," Medi Surgical Video, 1991.

Catagni, M.A., Malzev, V., Kirienko, A., "Advances in Ilizarov Apparatus Assembly—Fracture Treatment, Pseudarthroses–Lengthening Deformity Correction," Medicalplastic sri. 1994.

(Continued)

*Primary Examiner*—Darwin P Erezo
(74) *Attorney, Agent, or Firm*—Kilpatrick Stockton LLP

(57) ABSTRACT

A plate for use in fixating the position of a first bone segment relative to a second bone segment, the plate comprising a body portion having a plurality of attachment mechanisms located therein, wherein the attachment mechanisms include: a first group of three attachment mechanisms substantially positioned within 90°–150° of one another about a circle, and preferably within substantially 120° of one another, whereby the first group of attachment mechanisms is designed to facilitate attachment of a plurality of adjustable length struts to the plate; and a second group of attachment mechanisms substantially positioned about the circle that are designed to facilitate attachment of accessories to the plate, wherein the total number of the attachment mechanisms is a multiple of three.

29 Claims, 7 Drawing Sheets

U.S. PATENT DOCUMENTS

| | | | | |
|---|---|---|---|---|
| 2,487,989 | A | | 11/1949 | Sherburne |
| 3,176,805 | A | | 4/1965 | Gandy |
| 3,727,610 | A | | 4/1973 | Riniker |
| 3,941,123 | A | | 3/1976 | Volkov et al. |
| 3,977,397 | A | * | 8/1976 | Kalnberz et al. ..... 606/57 |
| 3,985,127 | A | | 10/1976 | Volkov et al. |
| 4,033,340 | A | | 7/1977 | Kalnberz |
| 4,100,919 | A | | 7/1978 | Oganesyan et al. |
| 4,112,935 | A | | 9/1978 | Latypov et al. |
| 4,127,119 | A | | 11/1978 | Kronner |
| 4,308,863 | A | | 1/1982 | Fischer |
| 4,361,144 | A | | 11/1982 | Slätis |
| 4,365,624 | A | | 12/1982 | Jaquet |
| 4,482,266 | A | | 11/1984 | Kaneko |
| 4,483,334 | A | | 11/1984 | Murray |
| 4,502,473 | A | | 3/1985 | Harris et al. |
| 4,541,422 | A | | 9/1985 | de Zbikowski |
| 4,554,915 | A | | 11/1985 | Brumfield |
| 4,570,625 | A | | 2/1986 | Harris et al. |
| 4,615,338 | A | | 10/1986 | Ilizarov et al. |
| 4,620,533 | A | | 11/1986 | Mears |
| 4,624,249 | A | | 11/1986 | Cambras |
| 4,628,922 | A | | 12/1986 | Dewar |
| 4,662,365 | A | | 5/1987 | Gotzen et al. |
| 4,768,524 | A | | 9/1988 | Hardy |
| 4,889,111 | A | | 12/1989 | Ben-Dov |
| 4,928,546 | A | | 5/1990 | Walters |
| 4,973,331 | A | | 11/1990 | Pursley et al. |
| 4,988,244 | A | | 1/1991 | Sheldon et al. |
| 5,028,180 | A | | 7/1991 | Sheldon et al. |
| 5,062,844 | A | | 11/1991 | Jamison et al. |
| 5,170,790 | A | | 12/1992 | Lacoste et al. |
| 5,179,525 | A | | 1/1993 | Griffis et al. |
| 5,180,380 | A | | 1/1993 | Pursley et al. |
| 5,209,750 | A | | 5/1993 | Stef |
| 5,259,710 | A | | 11/1993 | Charles |
| 5,275,598 | A | | 1/1994 | Cook |
| 5,354,158 | A | | 10/1994 | Sheldon et al. |
| 5,372,597 | A | | 12/1994 | Hotchkiss et al. |
| 5,388,935 | A | | 2/1995 | Sheldon |
| 5,405,347 | A | | 4/1995 | Lee et al. |
| 5,461,515 | A | | 10/1995 | Sorce |
| 5,466,085 | A | | 11/1995 | Sheldon et al. |
| 5,490,784 | A | | 2/1996 | Carmein |
| 5,702,389 | A | | 12/1997 | Taylor et al. |
| 5,728,095 | A | | 3/1998 | Taylor et al. |
| 5,776,132 | A | | 7/1998 | Blyakher |
| 5,797,908 | A | | 8/1998 | Meyers et al. |
| 5,971,984 | A | | 10/1999 | Austin et al. |
| 6,030,386 | A | | 2/2000 | Taylor et al. |

OTHER PUBLICATIONS

Chen, N., Song, S., "Direct Position Analysis of the 4–6 Stewart Platforms", *Journal of Mechanical Design,* vol. 116, Mar. 1994, pp. 61–66.

Chironis, Nicholas P., "Mechanisms & Mechanical Devices Sourcebook", pp. 366–367, McGraw–Hill, Inc., 1991.

Dasgupta, B., Mruthyunjaya, T.S., "A Canonical Formulation Of The Direct Position Kinematics Problem For A General 6–6 Stewart Platform", *Mech. Mach. Theory,* vol. 29, No. 6, 1994, pp. 819–827.

Dasgupta, B., Mruthyunjaya, T.S., "Letter To The Editor", *Mech. Mach. Theory,* vol. 29, No. 2, 1994, p. 341.

Fenton, R.G., "Response", *Mech. Mach. Theory,* vol. 29, No. 2, 1994, p. 343.

Fichter, E.F., "A Stewart Platform–Based Manipulator: General Theory and Practical Construction", *International Journal of Robotics Research,* vol. 5, No. 2, pp. 157–182.

Geng, Z.J., Haynes, L.S., "A "3–2–1" Kinematic Configuration Of A Stewart Platform And Its Application to Six Degree Of Freedom Pose Measurements", *Robotics & Computer–Integrated Manufacturing,* vol. 11, No. 1, 1994, pp. 23–24.

*Hex–Fix Surgical Technique* brochure, title page and pp. 1–7.

Ilizarov, Gavrill A., "Transosseous Osteosynthesis–Theoretical and Clinical Aspects of the Regeneration and Growth of Tissue," Springer–Verlag, 1992.

Ji, Z., "Dynamics Decomposition for Stewart Platforms", *Journal of Mechanical Design,* vol. 116, Mar. 1994, pp. 67–69.

Liu, K., Fitzgerald, J.M., Lewis, F.L., "Kinematic Analysis of a Stewart Platform Manipulator", *IEEE Transaction On Industrial Electronics,* vol. 40, No. 2, Apr. 1993, pp. 282–293.

Liu, K. Lewis, F.L. Fitzgerald, M., "Solution Of Nonlinear Kinematics Of A Parallel–Link Constrained Stewart Platform Manifulator", *Circuita Systems Signal Process,* vol. 13, No. 2–3, 1994, pp. 167–183.

*Monticelli Spinelli® External Fixation System,* cover and pp. 1–28.

Nair, R., Maddocks, J.H., "On The Forward Kinematics Of Parallel Manipulators", *The International Journal of Rototics Research,* vol. 13, No. 2, Apr. 1994, pp. 171–188.

Nanua, P., Waldron, K.J., and Murthy, V., "Direct Kinematic Solution of a Stewart Platform", *IEEE Transactions On Robotics And Automation,* vol. 6, No. 4, Aug. 1990, pp. 438–443.

Raghavan, M., "The Stewart Platform of General Geometry Has 40 Configurations", *Journal of Mechanical Design,* vol. 115, Jun. 1993, pp. 277–282.

Richards Medical Company, *Richards External Fixation Systems,* 1983, 8 pages.

Smith & Nephew Richards Inc., *The Original Ilizarov System. The Ilizarov External Fixator General Surgical Technique Brochure,* 1988.

Sreenivasan, S.V., Waldron, K.J., "Closed–Form Direct Displacement Analysis Of A 6–6 Stewart Platform", *Mech. Mach Theory,* vol. 29, No. 6, 1994, pp. 855–864.

Sloughton, R.S., Arai, T., "A Modified Stewart Platform Manipulator With Improved Dexterity", *IEEE Transactions On Robotics And Automation,* vol. 9, No. 2, Apr. 1993.

*Techniques In Orthopaedics, Basic Ilizarov Techniques,* vol. 5, No. 4, Dec. 1990, 4 pages.

The Ilizarov Method Bioskills Workshop Handbook, Essential Concepts & Methodology for Application of the Ilizarov Technique, 26 pages.

"The Ilizarov External Fixator, General Surgical Technique Brochure", 1988.

Varlax™, giddings & Lewis® Automation Technology, 4 pages.

Wen, F., Liang, C., "Displacement Analysis Of The 6–6 Stewart Platform Mechanisms", *Mech. Mach Theory,* vol. 29, No. 4, 1994, pp. 547–557.

Wohlhart, K., "Displacement Analysis Of The General Spherical Stewart Platform", *Mech. Mach. Theory,* vol. 29, No. 4, 1994, pp. 581–589.
Zhang, C., Song, S., "Forward Position Analysis Of Nealy General Stewart Platforms", *Journal of Mechanical Design,* vol. 116, pp. 54–60, Mar. 1994.
Zhuang, H., Roth, Z.S., "Method for Kinematic Calibration Of Stewart Platforms", *Journal Of Robotic Systems,* 10(3), 1993, pp. 391–405.

* cited by examiner

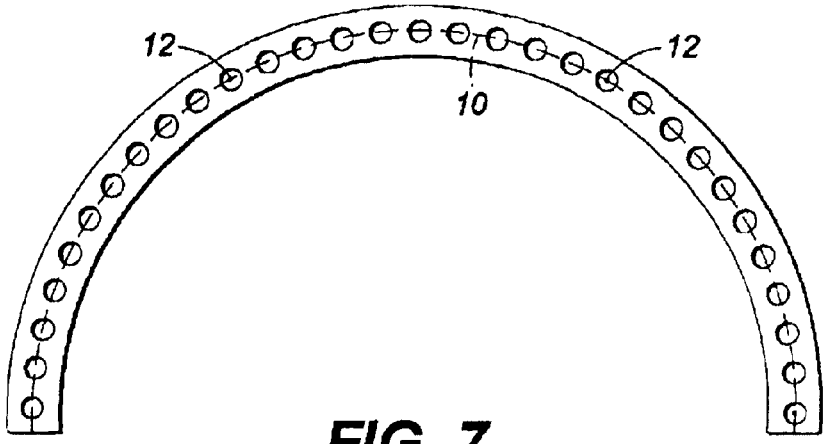
FIG. 7
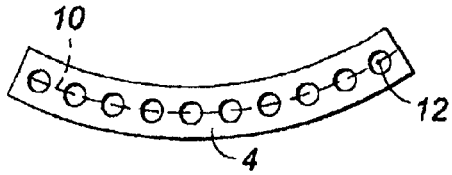
FIG. 8
FIG. 9
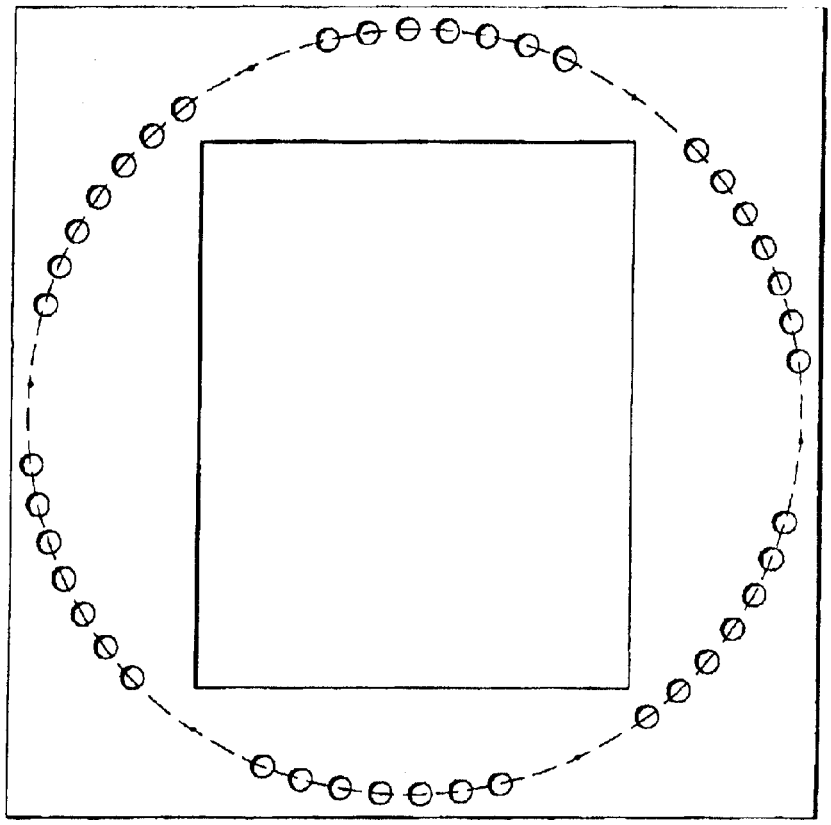

ORTHOPAEDIC FIXATION PLATE

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a plate for use as part of an external fixation device, and more particularly to a unique hole pattern within the plate.

2. General Background and Description of the Prior Art

Traditional circular ring external fixation devices consist of Ilizarov-type devices that are based on a circumferential external fixator system disclosed by G. A. Ilizarov during the early 1950's. The Ilizarov system includes at least two rings or "halos" that encircle a patient's body member (e.g., a patient's leg), connecting rods extending between the two rings, transfixion pins that extend through the patient's boney structure, and connectors for connecting the transfixion pins to the rings. Use of the Ilizarov system to deal with angulation, translation and rotation is disclosed in "Basic Ilizarov Techniques," Techniques in Orthopaedics®, Vol. 5, Nov. 4, December 1990, pages 55–59.

The Ilizarov system provides an external fixation frame that allows for gradual correction along and about six axes; however such frames require many parts and are relatively complicated to build and use in a clinical situation. In addition, often orthopedic external fixators such as Ilizarov frames must be modified after their initial application. Such modification may be necessary to convert from one correctional axis to another. Alternatively, such modifications may allow conversion from an initial adjustment type of frame to a weight bearing type frame, since some of the correctional configurations are not stable enough for weight bearing.

The rings used in the Ilizarov devices include a plurality of spaced apertures or holes that allow for the attachment of various accessories to the device. The pattern of Ilizarov ring holes is primarily determined as a function of the diameter of the ring. Conventional wisdom teaches that for any given diameter, the ring should include the maximum number of equally spaced arcuately positioned holes. Those skilled in the art believe that such hole positioning provides the surgeon with the greatest degree of flexibility in constructing the often times complicated and elaborate Ilizarov frame configuration. The Ilizarov ring holes, although equally spaced about a circle, are positioned such that the location of any given hole relative to another hole on additional rings attached thereto, is completely irrelevant.

Applicants have recently developed a new external fixation device known as the Taylor Spatial Frame™ external fixator. This device is described and claimed in the allowed U.S. patent application Ser. No. 08/782,731 entitled "Orthopaedic Fixation Device." In addition, applicants have developed a unique method of using the Taylor Spatial Frame™ fixator that is the subject of allowed U.S. patent application Ser. No. 08/726,713 entitled "Method of Using An Orthopaedic Fixation Device." Both of these patent applications are incorporated herein by reference. As disclosed in these prior patents, the Taylor Spatial Frame™ fixator, in its preferred embodiment, consists of two ring plates interconnected by six adjustable length struts. This device can be configured to correct virtually an infinite number of deformities, each of which would have otherwise required the construction of a specific custom Ilizarov frame.

As with the prior art Ilizarov fixator, the Taylor Spatial Frame™ fixator plates include a plurality of spaced apertures or holes therethrough for attaching accessories to the device. In addition, the plates include plurality of cavities or holes for attachment of the struts to the rings. Applicants have now developed a unique hole placement scheme for the Taylor Spatial FRAME™ fixator rings. This unique hole placement scheme takes advantage of the unique nature of the Taylor Spatial Frame™ fixator and the unique method of using the same, and provides substantial advantages over the unsystematically placed hole patterns utilized in Ilizarov rings.

SUMMARY OF THE INVENTION

It is an object of the present invention to provide a novel external fixation plate that can be used as part of the Taylor Spatial FRAME™ fixator, and facilitates the unique method of using the Taylor Spatial Frame™ fixator.

It is a further object of the present invention to provide a novel external fixation plate that easy to manufacture, and simplifies the fixator construction process.

It is a further object of the present invention to provide a novel external fixation plate that offers various clinical advantages over prior art designs by providing a convenient frame of reference to aid a surgeon in preoperative planning and surgical application of the device.

It is a further object of the present invention to provide a system of plates, wherein each plate within the system offers unique symmetrical properties and common hole spacing.

It is a further object of the present invention to provide a hole scheme for an external fixation plate that provides a clear geometric relationship between the holes on such plate relative to other holes on the same plate or holes on attached plates.

These and other objects are realized by a fixation plate that includes a plurality of attachment mechanisms located thereon. The attachment mechanism preferably consists of a plurality of equally spaced and symmetrically positioned holes. In accordance with a preferred embodiment, the present invention includes a plate having a body portion that includes a plurality of substantially equally spaced apertures or holes positioned arcuately therein. The holes are designed to facilitate attachment of a plurality of adjustable length struts that interconnect one or more plates, and the attachment of various accessories to the plates. The strut holes and the accessory holes may be indistinguishable or they may be different. The arrangement of the holes provides triple symmetry, and preferably 2×3 symmetry. Based on a defined geometric relationship between plate holes, a system of plates can be designed that offer triple symmetry or 2×3 symmetry.

BRIEF DESCRIPTION OF THE DRAWINGS

FIG. 7 is a top view of a plate in accordance with an alternative embodiment of the present invention.

FIG. 8 is a top view of a plate in accordance with an alternative embodiment of the present invention.

FIG. 9 is a top view of a plate in accordance with an alternative embodiment of the present invention.

DETAILED DESCRIPTION OF THE INVENTION

Because of the unique nature of the Taylor Spatial FRAME™ fixator and the unique method of using the Taylor Spatial FRAME™ fixator, the position of a given hole relative to another hole, either on the same plate or a different plate, is very important. Indeed, we have found that the correct positioning of the holes simplifies the manufacturing and device construction processes, simplifies the method of using the device by simplifying the geometric analysis of the system, and provides a number of clinical advantages.

Figure 1:
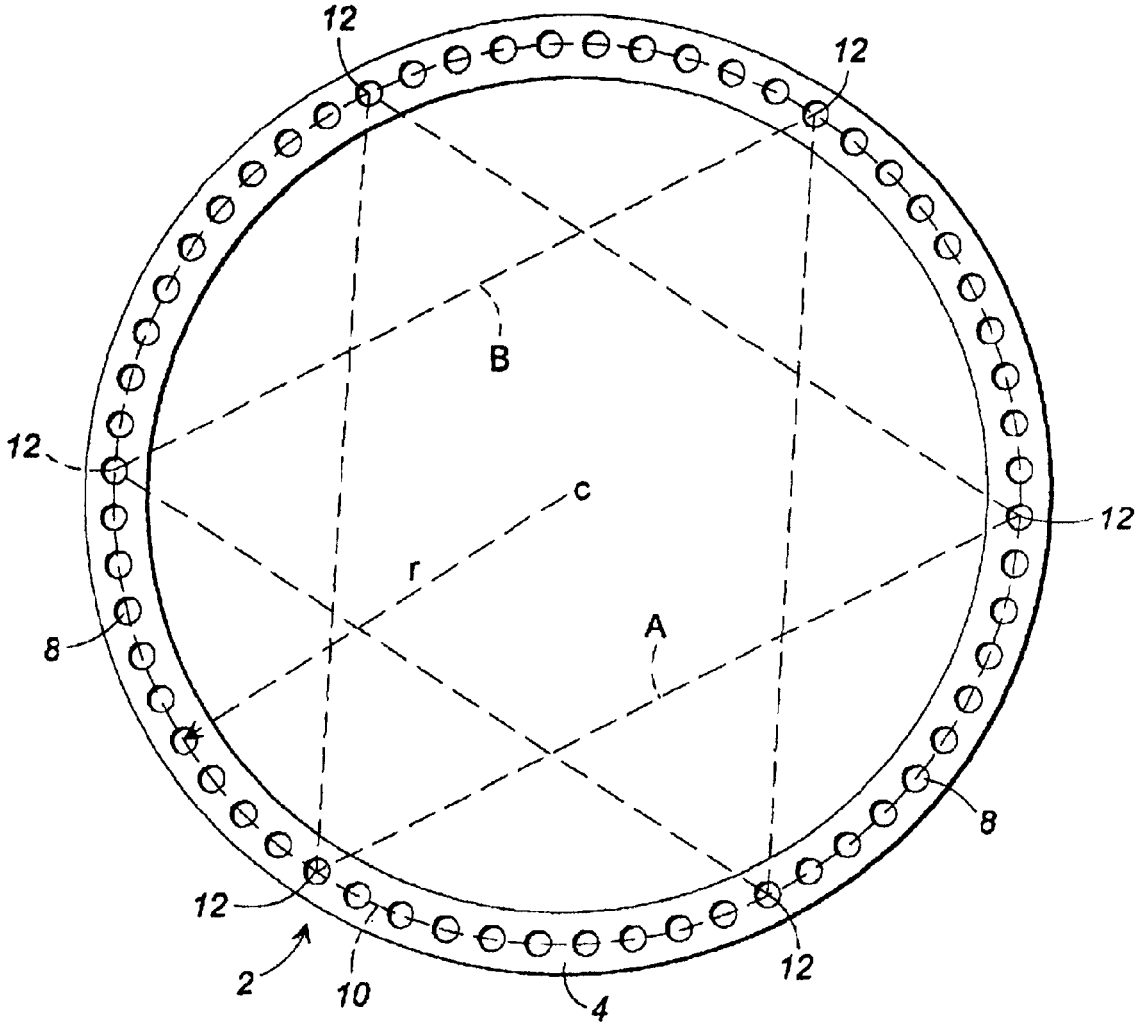
FIG. 1 is a top view of a plate in accordance with one embodiment of the present invention.

FIG. 1 illustrates a fixator plate in accordance with a preferred embodiment of the present invention. The plate 2 includes a circuit body portion 4 fabricated from a suitably strong and rigid material such as a metal, alloy, plastic, composite, or ceramic. The body portion 4 includes a plurality of substantially equally spaced apertures or holes 8 positioned arcuately therein. In the specific embodiment shown in FIG. 1, the center of the holes 8 form a complete circle as illustrated by the broken line 10, wherein the circle has a center c and a radius of r. It is important to note that each hole 8 may have a different diameter or shape as long as the center of the hole substantially intersects with the circle 10.

Figure 2:
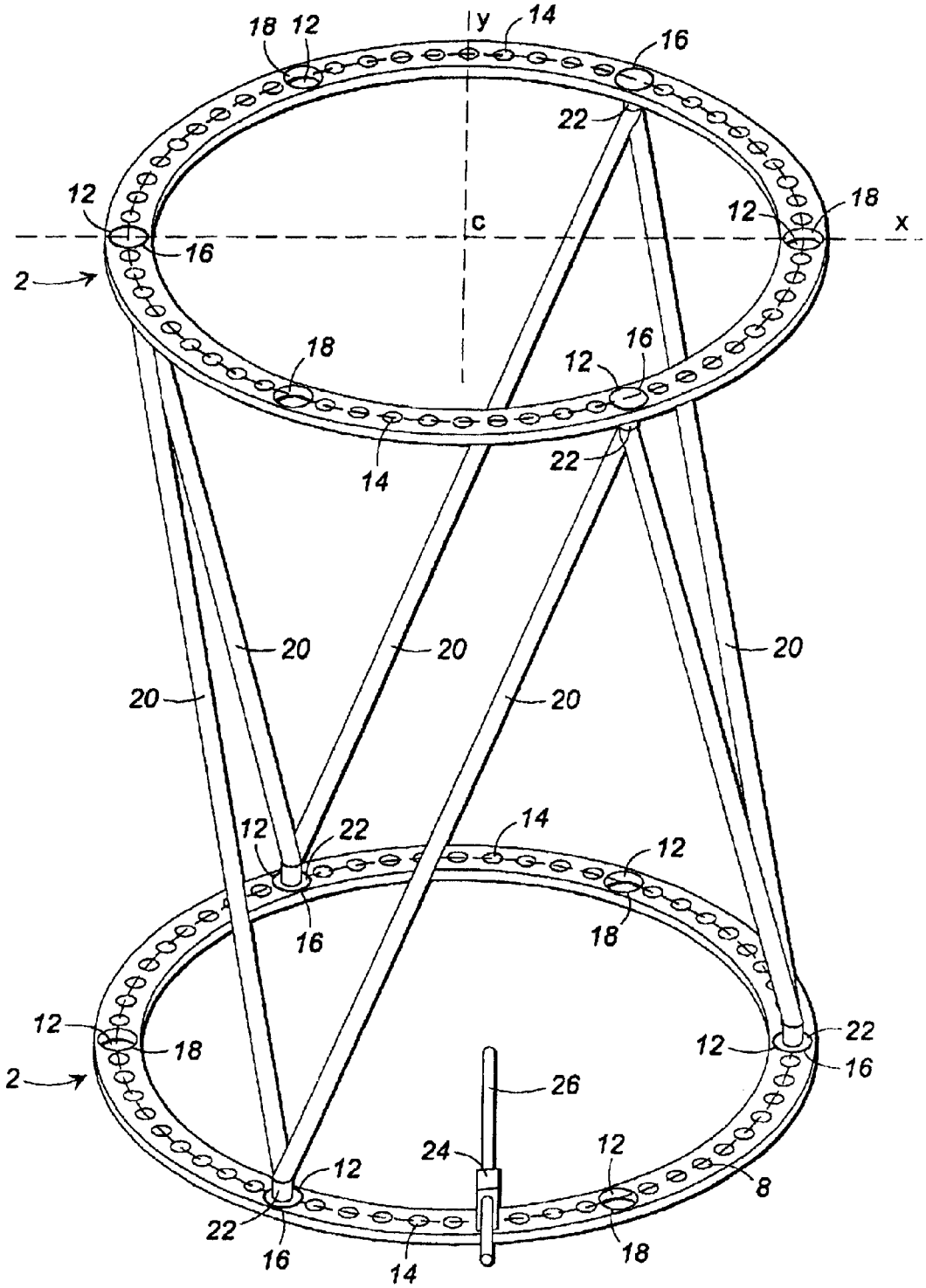
FIG. 2 is a perspective view of an external fixation device incorporating one embodiment of the novel plate of the present invention.
Figure 4:
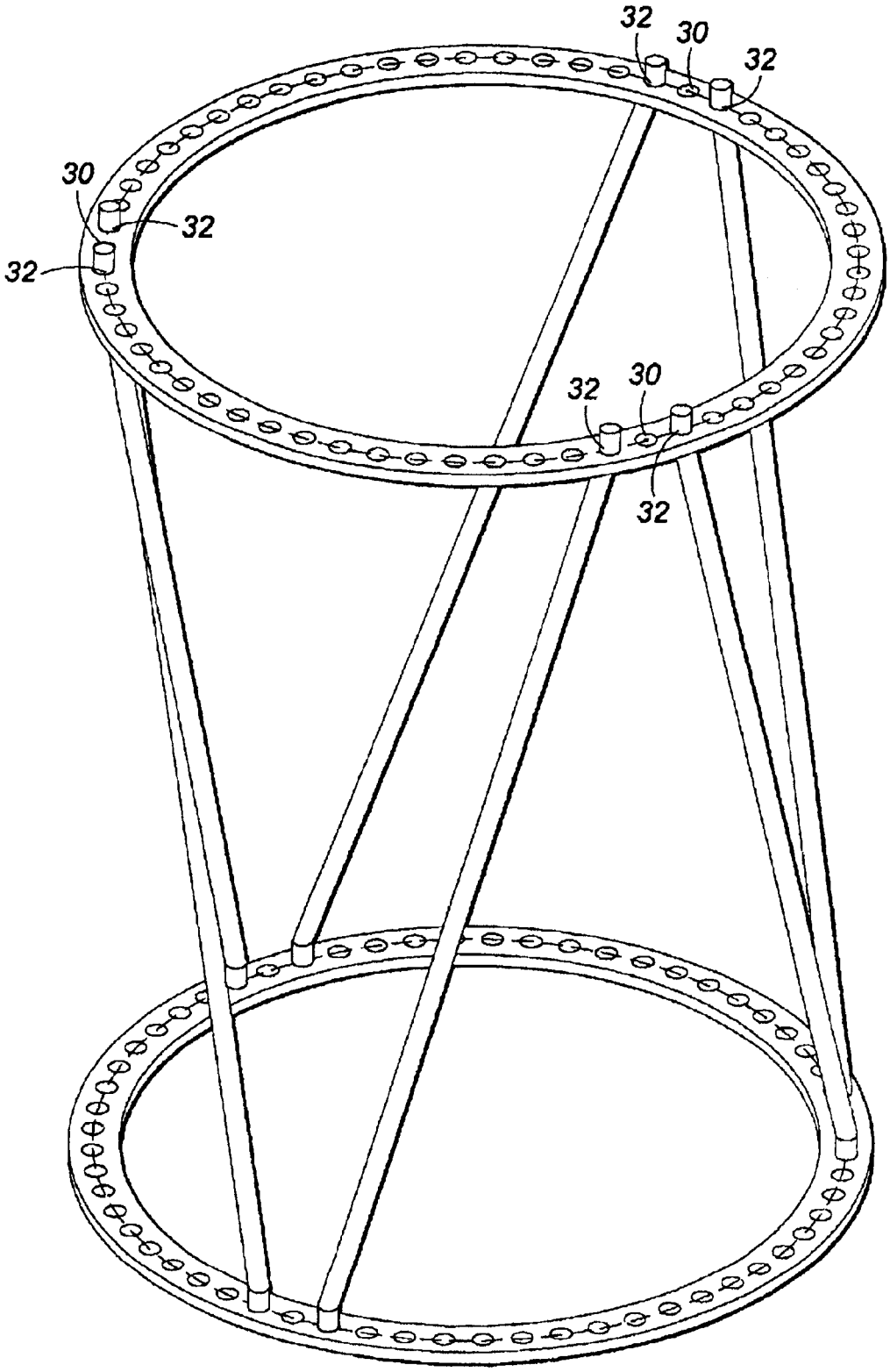
FIG. 4 is a perspective view of an external fixation device incorporating an alternative embodiment of the novel plate of the present invention.

As illustrated in FIG. 2 and FIG. 4, the holes 8 are designed to facilitate attachment of a plurality of adjustable length struts 20 that interconnect one or more plates 2. In accordance with the preferred embodiment of the present invention, six struts 20 are used to interconnect two plates 2. In addition, the holes 8 are designed to facilitate attachment of various accessories to the plate 2, such as for example, wires (not shown), clamps 24, pins 26, additional plates, etc. In accordance with the embodiment shown in FIG. 1 and FIG. 4, the strut holes and the accessory holes are indistinguishable, i.e. any hole 8 can be selected to serve as a strut hole or an accessory hole. In accordance with an alternative embodiment, as shown in FIG. 2, the accessory holes 14 and the strut holes 12 are different.

As illustrated in FIG. 2, in accordance with one embodiment of the present invention, each plate 2 has three actual strut attachment positions 16. In addition, each plate 2 includes three additional strut positions 18 that are not actually used. The unused strut positions 18 are included to provide a 2×3 symmetrical design, which is discussed in greater detail below. In the preferred embodiment of the invention as shown in FIG. 2, the used strut attachment holes 16 should be positioned approximately 120° from one another so as to form a substantially equilateral triangle. Similarly, the unused strut attachment holes 18 should be positioned approximately 120° from one another so as to form a second substantially equilateral triangle. The two overlapping triangles are illustrated by broken lines in FIG. 1, and are designated triangle A and triangle B. Alternatively, one or more strut attachment holes 16, 18 can deviate slightly from its ideal 120° position. Such deviation, however, should be less than 30°, but preferably no more than 15°, and ideally less than 6°.

Unlike the unsystematically positioning of prior art Ilizarov ring holes, the holes 8 in the present device are preferably strategically positioned within plate 2 to provide 2×3 symmetrically throughout a complete system of plates. 2×3 symmetry is achieved when the holes are positioned such that the plate can be rotated in increments of 180° about a first axis and increments of 120° about a second axis, and each time maintain identical hole positions. For example, the plate 2 can be rotated 180° about an axis passing through center c and within the plane of the plate 2, i.e. the x axis shown in FIG. 2. Such a rotation would essentially flip plate 2 over. For both of the two possible positions, the hole pattern within plate 2 would be identical. This characteristic represents the "2" of the 2×3 symmetry. Similarly, plate 2 can be rotated in increments of 120° about an axis perpendicular to the plate and passing through center c, i.e. the y axis shown in FIG. 2. There are three possible positions that the plate 2 could assume by making 120° rotation about the y axis. Following each rotation, however, the resulting hole positions will remain unchanged. This characteristic represents the "3" of the 2×3 symmetry. In accordance with the present invention, a system of plates is provided, as described hereinbelow, wherein each plate within the system offers at least triple symmetry (i.e., the "3" symmetry), and preferably each plate offers complete 2×3 symmetry.

In order to obtain the 2×3 symmetry, as noted above, plate 2 should include two sets of three strut holes with each strut hole 12 positioned about 60° apart in a circle. In addition, 2×3 symmetry requires that the total number of holes 8 (including both strut holes 12 and accessory holes 14) be a multiple of six (6). For triple symmetry alone, however, the total number of holes 8 need only be a multiple of three (3). Furthermore, the accessory holes should be equally spaced. One skilled in the art will appreciate that asymmetrical "dummy" holes can be added to the plate 2. Such a plate would nonetheless fall within the scope of the present invention.

Figure 3:
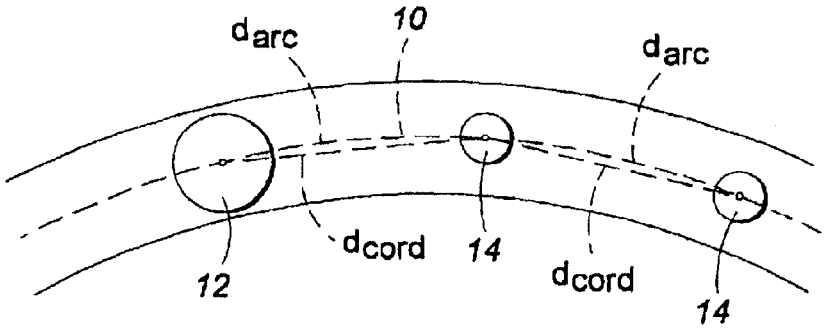
FIG. 3 is an enlarged view of a portion of one of the plates shown in FIG. 2.

As illustrated in FIG. 3, the spacing between the accessory holes 14 can be measured in terms of the arc length $l_{arc}$ along circle 10 or in terms of the chord length $l_{chord}$. In accordance with the preferred embodiment, the distance between holes 14 is measured by the chord length $I_{chord}$, and such lengths are equal. Furthermore, the distance between each strut hole 12 and its adjacent accessory hole 14 need not be the same as the distance between two adjacent accessory holes 14. As illustrated in FIG. 3, this distance can be measured along arc as $d_{arc}$ or along the chord as decor. In accordance with the preferred embodiment of the present invention, the chord lengths between every accessory hole 14 and its adjacent accessory hole 14 or strut hole 12 are equal, that is $d_{chord}=l_{chord}$. In addition, the chord length is should be greater than about 0.475 inch, but preferably is between about 0.48–0.52 inch, and most preferably equal to about 0.5 inch.

In accordance with the specific embodiment of the present invention illustrated in FIG. 2, the exact positions of the holes 8 are determined as follows. The process is very different from the unsystematic positioning of the holes in prior art Ilizarov devices, which starts with determining the ring diameter. The Taylor Spatial Frame™ fixator hole positions are determined by first determining the hole spacing, and then determining the number of holes that will be used. The present hole positioning scheme starts with the number of holes because it is important that the number be a multiple of three to maintain the requisite symmetry. Once the distance between the holes and the number of holes is determined, the diameter of the ring is defined by the formula:

$$\text{diameter} = l\left(\sqrt{\left(\frac{1}{\tan^2\left(\frac{180}{N}\right)} + 1\right)}\right)$$

where l is the chord distance between holes 8, and N is the total number of holes.

Figure 5:
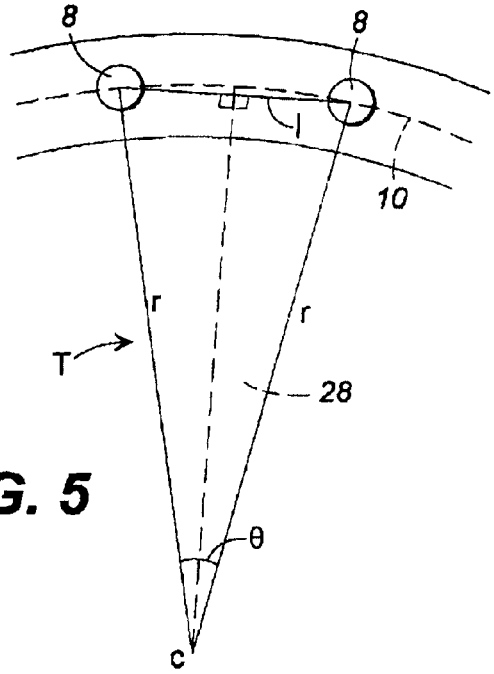
FIG. 5 is an enlarged view of a portion of a plate of the present invention, and illustrates the geometric relationship between two adjacent holes.

As illustrated in FIG. 5, for any given two adjacent holes 8, the angle between the holes is θ, and the chord between the holes is 1. An isosceles triangle T is formed by connecting the two adjacent plate holes 8 and the center c of the circle 10. If a line 28 having length b is formed in the middle of the isosceles triangle T, two right triangles are formed, and the following relationships exists:

$$b^2 + (1/2l)^2 = r^2 \quad (1)$$

and $$\text{TAN}(1/2\theta) = \frac{1/2l}{b} \quad (2)$$

where r represents the radius of the circle 10. If for convenience we define v=½l and Q=tan (½θ), the following relationships can be derived from the above equations:

From Equation (1)

$$b^2 = r^2 - v^2 \quad (3)$$

$$b = \sqrt{r^2 - v^2} \quad (4)$$

From Equation (2)

$$Q = \frac{v}{b} \quad (5)$$

Combining (4) and (5)

$$Q = \frac{v}{\sqrt{r^2 - v^2}} \quad (6)$$

solving for the radius r gives:

$$r = \sqrt{\frac{v^2}{Q^2} + v^2} \quad (7)$$

or $$r = \sqrt{v^2\left(\frac{1}{Q^2} + 1\right)}$$

Therefore, for any plate having N holes and a chord distance of 1 between adjacent holes, the diameter of the circle that defines the hole locations can be expressed mathematically as $$\text{diameter} = 2\left(\sqrt{\left(\frac{1}{2}\right)^2\left(\frac{1}{\tan^2(1/2\theta)} + 1\right)}\right) \quad (8)$$

$$= l\left(\sqrt{\left(\frac{1}{\tan^2(1/2\theta)} + 1\right)}\right) \quad (9)$$

If the total number of holes in the ring will be N, then θ=360°/N, and $$\text{diameter} = l\left(\sqrt{\left(\frac{1}{\tan^2\left(\frac{180}{N}\right)} + 1\right)}\right) \quad (10)$$

Using the relationship defined in equation 10, a system of rings including a variety of ring diameters can be developed wherein each ring has triple symmetry and the hole spacing for each ring is the same. The following table illustrates such a system wherein the hole spacing in 0.5 inch:

TABLE I

| Chord Length (l) (inches) | Number of Holes (N) | Diameter (inches) | angle (θ) (degrees) |
|---|---|---|---|
| 0.5 | 3 | 0.5776 | 130 |
| 0.5 | 6 | 1.0030 | 60 |
| 0.5 | 9 | 1.4519 | 40 |
| 0.5 | 12 | 1.9319 | 30 |
| 0.5 | 15 | 2.4049 | 24 |
| 0.5 | 18 | 2.8794 | 20 |
| 0.5 | 21 | 3.3548 | 17.143 |
| 0.5 | 24 | 3.8306 | 15 |
| 0.5 | 27 | 4.3069 | 13.333 |
| 0.5 | 30 | 4.7834 | 12 |
| 0.5 | 33 | 5.2601 | 10.939 |
| 0.5 | 36 | 5.7369 | 10 |
| 0.5 | 39 | 6.2138 | 9.281 |
| 0.5 | 42 | 6.6907 | 8.571 |
| 0.5 | 45 | 7.1678 | 8 |
| 0.5 | 48 | 7.6449 | 7.5 |
| 0.5 | 51 | 8.1220 | 7.059 |
| 0.5 | 54 | 8.5992 | 6.657 |
| 0.5 | 57 | 9.0764 | 6.316 |
| 0.5 | 60 | 9.5537 | 6 |
| 0.5 | 63 | 10.0309 | 5.714286 |
| 0.5 | 66 | 10.5082 | 5.454545 |
| 0.5 | 69 | 10.9855 | 5.217391 |
| 0.5 | 72 | 11.4628 | 5 |
| 0.5 | 75 | 11.9401 | 4.8 |
| 0.5 | 78 | 12.4174 | 4.615385 |
| 0.5 | 81 | 12.8948 | 4.444444 |
| 0.5 | 84 | 13.3721 | 4.285714 |
| 0.5 | 87 | 13.8497 | 4.137931 |
| 0.5 | 90 | 14.3269 | 4 |
| 0.5 | 93 | 14.8042 | 3.870968 |
| 0.5 | 96 | 15.2816 | 3.75 |
| 0.5 | 99 | 15.7590 | 3.635364 |
| 0.5 | 102 | 16.2364 | 3.529412 |
| 0.5 | 105 | 16.7138 | 3.428571 |
| 0.5 | 108 | 17.1912 | 3.333333 |
| 0.5 | 111 | 17.6686 | 3.243243 |
| 0.5 | 114 | 18.1460 | 3.157895 |
| 0.5 | 117 | 18.6234 | 3.076923 |
| 0.5 | 120 | 19.1008 | 3 |
| 0.5 | 123 | 19.5782 | 2.826829 |
| 0.5 | 126 | 20.0556 | 2.857143 |
| 0.5 | 129 | 20.5330 | 2.790698 |

The triple symmetry for the complete system is realized by only including rings where the numbers of holes in each plate is a multiple of three. Similarly, a system with complete 2×3 symmetry can be designed by using plates where the number of holes in each plate is a multiple of six.

As noted above, the arc length, as opposed to the chord length, between adjacent holes 8 can be fixed. If the arc length between the holes 8 is fixed, for a given arc length k and holes N, the circumference of the circle 10 will equal k×N. Therefore the diameter would be:

$$\text{diameter} = kN/\pi$$

Using this relationship, a plate system such as following can be made:

TABLE II

| Arc Length (inches) | Number of Holes | Diameter (inches) |
|---|---|---|
| 0.5 | 6 | 0.9549 |
| 0.5 | 9 | 1.4324 |
| 0.5 | 12 | 1.9099 |
| 0.5 | 15 | 2.3873 |
| 0.5 | 18 | 2.8648 |
| 0.5 | 21 | 3.3423 |
| 0.5 | 24 | 3.8197 |
| 0.5 | 27 | 4.2972 |
| 0.5 | 30 | 4.7746 |
| 0.5 | 33 | 5.2521 |
| 0.5 | 36 | 5.7296 |
| 0.5 | 39 | 6.2070 |
| 0.5 | 42 | 6.6845 |
| 0.5 | 45 | 7.1620 |
| 0.5 | 48 | 7.6394 |
| 0.5 | 51 | 8.1169 |
| 0.5 | 54 | 8.5944 |
| 0.5 | 57 | 9.0718 |
| 0.5 | 60 | 9.5493 |
| 0.5 | 63 | 10.0268 |
| 0.5 | 66 | 10.5042 |
| 0.5 | 69 | 10.9817 |
| 0.5 | 72 | 11.4592 |
| 0.5 | 75 | 11.9366 |
| 0.5 | 78 | 12.4141 |
| 0.5 | 81 | 12.8916 |
| 0.5 | 84 | 13.3690 |
| 0.5 | 87 | 13.8465 |
| 0.5 | 90 | 14.3239 |
| 0.5 | 93 | 14.8014 |
| 0.5 | 96 | 15.2789 |
| 0.5 | 99 | 15.7563 |
| 0.5 | 102 | 16.2338 |
| 0.5 | 105 | 16.7113 |
| 0.5 | 108 | 17.1887 |
| 0.5 | 111 | 17.6662 |
| 0.5 | 114 | 18.1437 |
| 0.5 | 117 | 18.6211 |
| 0.5 | 120 | 19.0986 |
| 0.5 | 123 | 19.5761 |
| 0.5 | 126 | 20.0535 |
| 0.5 | 129 | 20.5310 |

Figure 6:
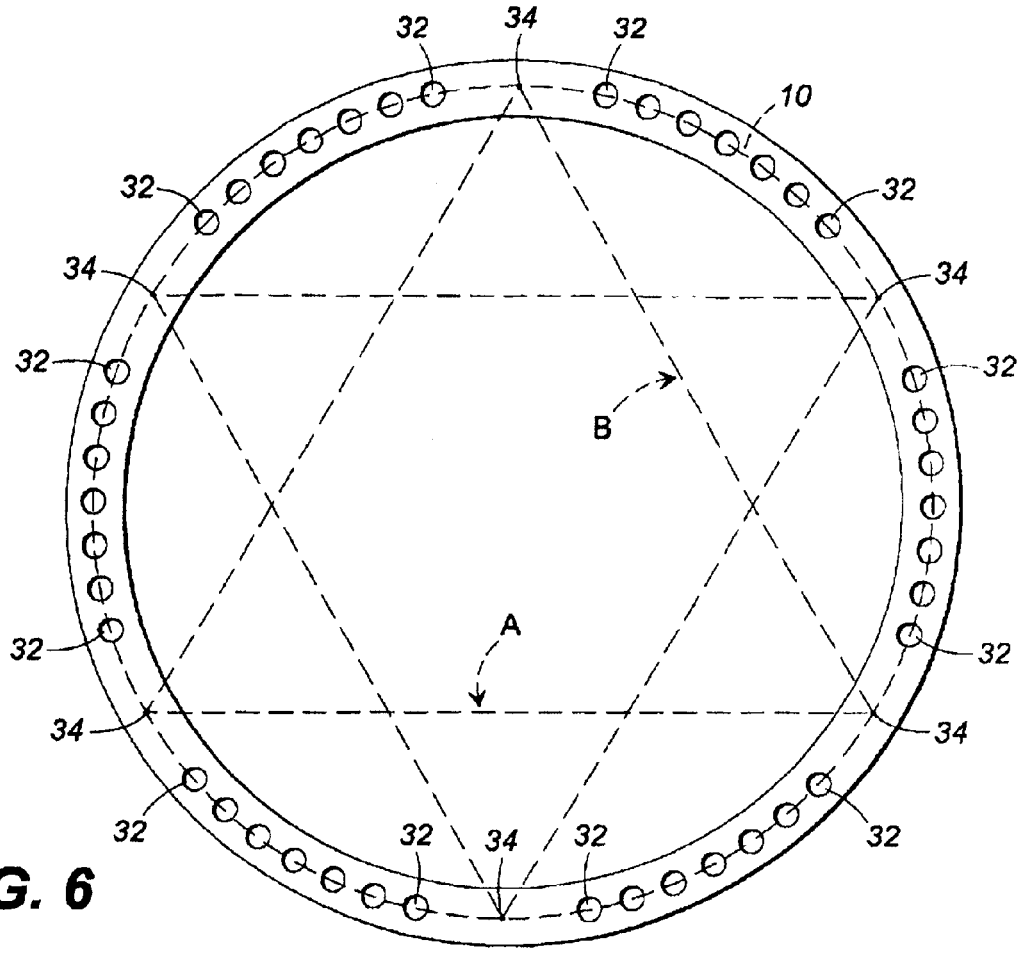
FIG. 6 is a top view of a plate in accordance with an alternative embodiment of the present invention.

FIG. 4 illustrates an alternative embodiment of the present invention. Unlike the embodiment illustrated in FIG. 2, the adjoining struts 20 in FIG. 4 do not connect to the plates 2 at a single common hole 8. As a result, each plate 2 in FIG. 4 includes six (6) strut holes 32 that are connected to a strut 20. As illustrated, the adjacent connecting strut holes 32 are separated by a single unused hole 30. In other embodiments of the present invention, the adjacent connecting strut holes 32 may be separated by no holes or by more than one unused hole 30. When adjacent struts 20 do not terminate at a common hole a theoretical strut hole should be determined. As illustrated in FIG. 6, the theoretical strut hole 34 is positioned along the arc of circle 10 half way between the two actual strut holes 32, i.e. along the circle 10 at the bisector of the two actual strut holes. When adjacent struts terminate at a single strut hole as in FIG. 2, the theoretical strut hole is the actual strut hole. In accordance with the present invention, the theoretical strut holes 34 on plate 2 should form two overlapping triangles A, B in the same manner described above regarding the embodiment illustrated in FIG. 2. As with the actual strut holes, the chords connecting the theoretical strut holes 34 preferably form two substantially equilateral triangles. The theoretical strut holes 34, however, may deviate from their ideal 120° positions to the same extent described above with regard to actual strut holes.

The extent to which an actual strut hole 32 can deviate from its theoretical strut hole is limited. As this deviation increases, the range of movement between the two plates 2 is reduced. The reduced range limits the various configurations that the device can assume, and therefore, limits the types of deformities that can be corrected with the device. As a result, the deviation of an actual strut hole 32 from its theoretical strut hole should be less than about 30°, but can be less than 12°, and preferable no more than about 6°.

The hole spacing scheme of the present invention can be utilized to design plates having holes that do not form a complete circle. For example, a half plate or a ⅙ plate, as illustrated in FIGS. 7 and 8 respectively, can be designed. In addition, the plate itself need not be circular, as illustrated in the embodiment shown in FIG. 9.

The mathematical relationships between hole spacing, the number of holes and the diameter that are set forth above specifically relate to a hole pattern that forms a complete circle and includes equally spaced hole around the entire circle. These mathematical relationships, however, can be adapted to describe the hole pattern for a partial circle. For example, assume that you wanted n holes positioned about a partial ring that has an arc length of $\alpha°$, i.e. 180° for a half ring, 90° for a quarter ring, etc. The number of such partial rings required to form a complete circle would be $360/\alpha$. The number of holes in such a theoretical circle (N) equals $n(360/\alpha)$. One would then use the number of holes for the theoretical complete ring (N) in the equations set forth above to define the hole positions needed to form the requisite partial plate.

Figure 10:
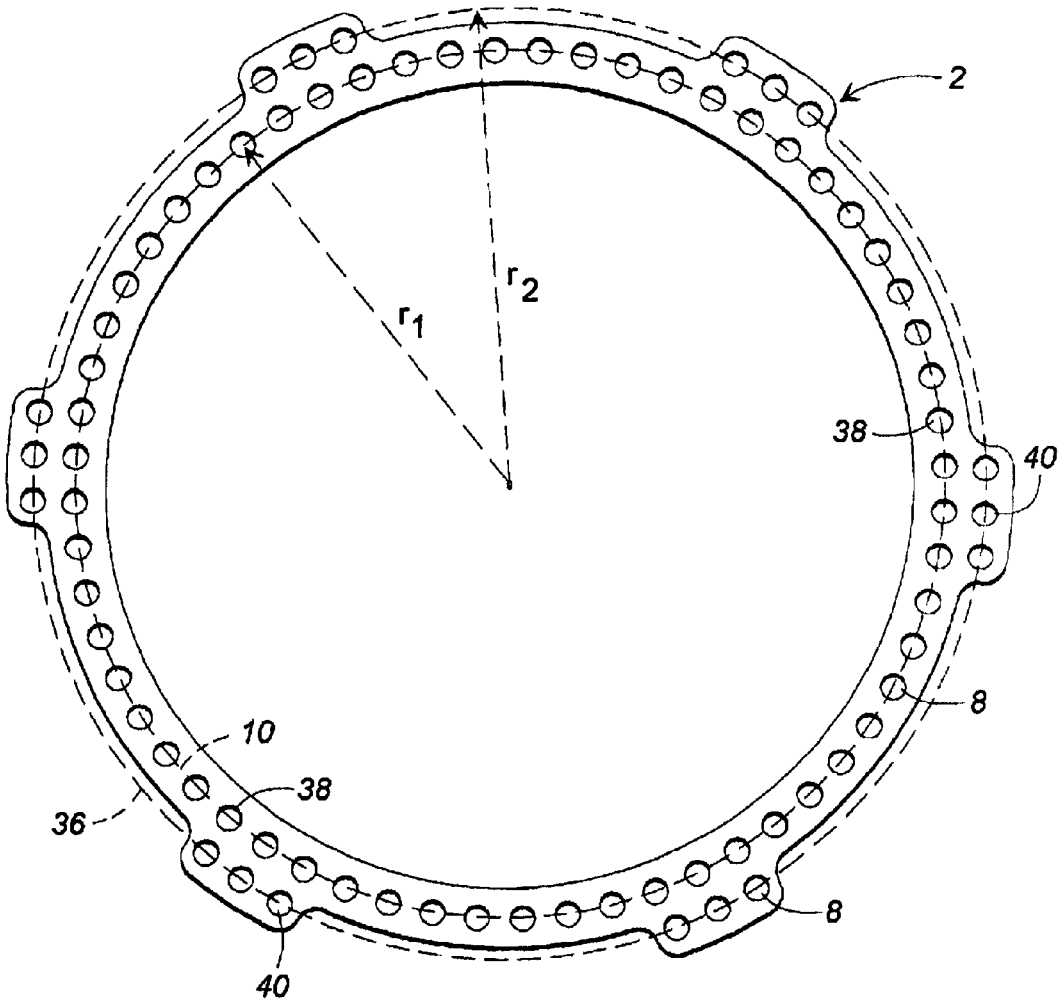
FIG. 10 is a top view of a plate in accordance with an alternative embodiment of the present invention.

In accordance with another embodiment of the present invention, a plate can include holes corresponding to more than one diameter within a given system. As noted above each system is defined by the hole spacing. An example is illustrated in FIG. 10 using the system defined above in Table I. The plate 2 includes two sets of holes 8. The first set 38 includes sixty (60) holes equally spaced ($l_{chord}$–0.5 inch) along circle 10. As indicated above in Table I, the diameter of circle 10 is 9.5537 inches, and the radius $r_1$=4.7769 inches. The second set of holes 40 consists of six groups of three holes, i.e. six partial plates. These hole are spaced along the next highest diameter within the system. Therefore, the diameter of circle 36 is 10.5082 and the radius $r_2$=5.2541. Multiple diameter plates, such as shown in FIG. 10 are very useful. In such plates, the struts can be attached at one diameter, using for example hole set 40, and the accessories can be attached using the other diameters, using for example hole set 38.

Figure 11:
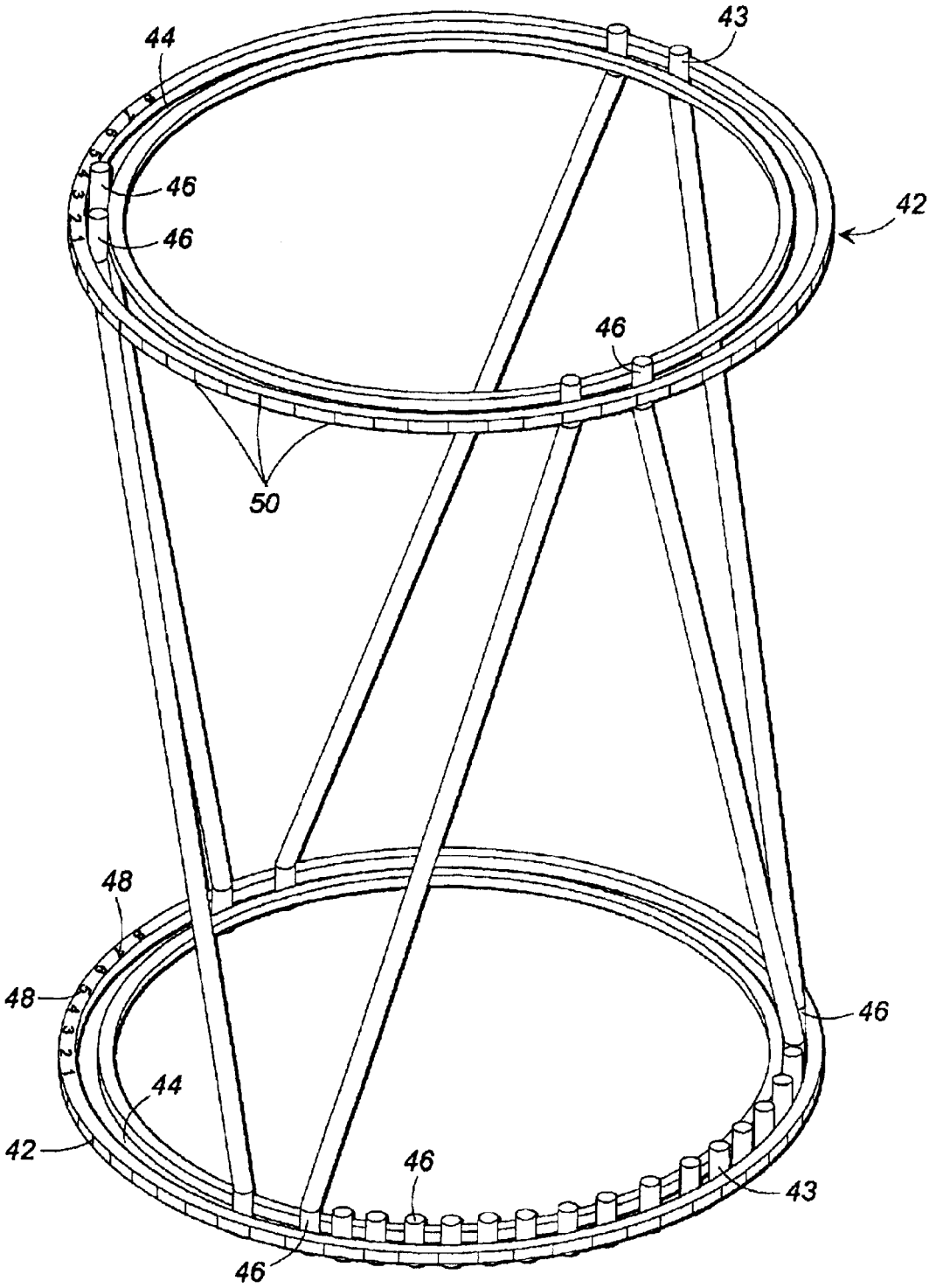
FIG. 11 is a perspective view of an external fixation device incorporating an alternative embodiment of the novel plate of the present invention.

It is important to emphasize that although the present invention is described in terms of accessory holes and strut holes, other attachment mechanisms can be used and still fall within the scope of the present invention. For example, each hole could be replaced with a peg that would facilitate attachment of a strut or accessory. Alternatively, an illustrated in FIG. 11, the plate 42 could include one continuous circular grove 44 that traces circle 10. Clamps 46 could be provided that attach to the groove 44 at any location. Such clamps 46 can easily be positioned to mimic the hole patterns described above. Indeed, such a plate 42 could included indicia such as markings 48 or etches 50 within the plate, that designate the hole positions described above.

The unique hole placement scheme described herein provides a number of advantages over the prior art. In particular, a ring that has 2×3 symmetry substantially simplifies the manufacturing process and the fixator construction process. With 2×3 symmetrical rings, one ring can serve as either the upper ring or the lower ring. As a result, a manufacturer need only make half as many ring designs for a system. In addition, if a surgeons using the device want to attach additional rings to the base Taylor Spatial Frame™ fixator, they need not overly concern themselves with having the proper ring, nor the proper orientation of the ring.

Key advantages also result from having a defined relationships between the various holes on a plate, and a defined relationship between various holes on different plates. In general, this facilitates the use of mathematical methods to analyze a fixation system, and determine the proper mode for correcting a deformity. From a clinical standpoint, it gives a surgeon a great deal of flexibility and aids in preoperative planning and surgical application of the device. For example, in cases of sever deformities the various bone fragments are completely out of alignment. In such cases it is difficult for a surgeon to place various plates with the same orientation on the various fragments. With the current invention, a surgeon when attaching the device can place reference wires at the same predetermined anatomical position on each unaligned bone fragment. One the surgeon determines the appropriate positioning of the first plate on the first bone fragment, the first plate is secured to the reference wire. Subsequent plates can then be easily positioned on the remaining bone fragments. A surgeon would attached the subsequent plates to the reference wires on the remaining fragments using the accessory holes at the same locations used with the first plate. The various plates would then be aligned after the correction is made. Such strategic placement of plates relative to one another facilitates the use of the unique method of using the Taylor Spatial FRAME™ fixator. Moreover, this provides an easy gauge during the course of the correction that allows the surgeon to judge if the correction is accurate or needs adjustment. Indeed, if the plate holes are not moving into alignment, the surgeon knows that an adjustment is needed. Furthermore, once the plates have returned to their neutral positions, with the holes in the upper and lower plates are perfectly aligned, and a surgeon can simply insert horizontal rods. Such rods could provide accessory stabilization if required.

We claim:

1. An orthopaedic spatial fixation system for holding bone parts comprising a plurality of fixation plates wherein each plate includes a body portion having n [holes] *attachment structures* positioned therein, whereby said [holes] *attachment structures* are substantially positioned along an arc of $\alpha°$ of a circle defined by a diameter d, and [the cord] *a chord* length between adjacent [holes] *attachment structures* is [substantial] *substantially* equal to [1] *and is substantially equal between all attachment structures*, and $$d = l\left(\sqrt{\frac{1}{\tan^2\left(\frac{\alpha}{2n}\right)} + 1}\right)$$

[and] whereby [the diameter d for each plate within the system is unique, and] the value for $n(360/\alpha)$ [for each consecutive plate diameter d] in the system is a multiple of 3*, and*

*wherein at least two of the fixation plates are connected to each other by at least six substantially rigid, adjustable length struts, wherein each of the struts is disposed substantially diagonally with respect to its adjacent struts.*

2. The orthopaedic spatial fixation system of claim 1 further comprising bone pins for interfacing the bone parts and plates; and,

[a plurality of] *wherein the* struts [that] extend between the plates to hold the plates in a selected position relative to one another and relative to the bone parts;

wherein the struts are attached to the plates at the [holes] *attachment structures*; and, wherein [a plurality of] the struts have adjustable length sections for varying the length of the strut to adjust the relative position of the plates.

3. The orthopaedic spatial fixation system of claim 2 wherein the [holes] *attachment structures* on at least one of the plates are one hundred twenty degrees (120°) apart.

4. The orthopaedic spatial fixation system of claim 1 wherein rotation of one plate one hundred twenty degrees (120°) relative to an adjacent plate results in the same alignment of adjacent [holes] *attachment structures* as before such rotation of the plates.

5. The orthopaedic spatial fixation system of claim 1 wherein the plates are symmetrically configured so that if one plate is placed over an adjacent plate, the [holes] *attachment structures* in each plate can be aligned.

6. The orthopaedic spatial fixation system of claim 5 wherein the plates are symmetrically configured so that one plate can be flipped over without affecting the alignment of adjacent [holes] *attachment structures*.

7. The orthopaedic spatial fixation system of claim 2 wherein there are two plates and each plate includes 3 [holes] *attachment structures*.

8. The ort*h*opaedic spatial fixation system of claim 7 wherein

[there are] *the struts comprise only* six struts each having a first end and a second end;

the first end of each strut is attached to one of the plates and the second end of each strut is attached to the other plate;

the ends of the struts are attached to the plates at the [holes] *attachment structures*; and, each [hole] *attachment structure* accommodates two strut ends, one from each of two adjacent struts.

*9. The orthopaedic spatial fixation system of claim 1, wherein the attachment structures are holes.*

*10. The orthopaedic spatial fixation system of claim 1, wherein the circle comprises a groove and the attachment structures are clamps attached to the groove.*

*11. The orthopaedic spatial fixation system of claim 1, further comprising markings or etches to designate the attachment structure positions.*

*12. The orthopaedic spatial fixation system of claim 1, further comprising one or more plates being multiple diameter plates having a second set of attachment structures.*

*13. The orthopaedic spatial fixation system of claim 12, wherein the second set of attachment structures is not spaced according to the diameter equation and chord length limitations.*

*14. The orthopaedic spatial fixation system of claim 1, wherein the chord length between adjacent attachment structures is between about 0.48 inches and about 0.52 inches.*

*15. An orthopaedic spatial fixation system, comprising a plurality of arcuate shaped fixation plates, wherein each plate comprises a plurality of attachment structures, at least some of which have substantially uniform sizes and a geometrical arrangement defined whereby the attachment structures are: (a) in sets of three, (b) spaced substantially 120 degrees apart from each other along an arc of the fixation plate, and (c) substantially equally spaced apart; wherein rotating a first one of the fixation plates substantially 120 degrees from a starting position in a plane substantially parallel to another one of the fixation plates causes the first fixation plate to present the same geometrical arrangement of attachment structures as the geometrical arrangement of the attachment structures of the another plate, and*

*wherein at least two of the fixation plates are connected to each other by at least six substantially rigid, adjustable*

*length struts, wherein each of the struts is disposed substantially diagonally with respect to its adjacent struts.*

*16. The orthopaedic spatial fixation system of claim 15, whereby rotating the first fixation plate substantially 60 degrees from the starting position in a plane substantially parallel to another one of the fixation plates presents the same geometrical arrangement of attachment structures as the geometrical arrangement of the attachment structures of the another plate.*

*17. The orthopaedic spatial fixation system of claim 15, wherein the number of attachment points is a multiple of six, providing 2×3 symmetry.*

*18. The orthopaedic spatial fixation system of claim 15, wherein at least one of the fixation plates is ring shaped.*

*19. The orthopaedic spatial fixation system of claim 15, wherein the plurality of attachment structures is positioned such that in use, at least some of the attachment structures on one of the plates move into alignment with at least some of the attachment structures on another plate as adjustment is effected.*

*20. The orthopaedic spatial fixation system of claim 15, wherein the attachment structures are positioned along an arc of α° of a circle defined by a diameter d, and a chord length between adjacent attachment structures is substantially equal to l, and the defined relationship comprises*

$$d = l\left(\sqrt{\frac{1}{\tan^2\left(\frac{\alpha}{2n}\right)} + 1}\right)$$

*21. The orthopaedic spatial fixation system of claim 15, wherein the orthopaedic spatial fixation system is adapted to be positioned on a patient.*

*22. The orthopaedic spatial fixation system of claim 15, wherein the struts comprise only six adjustable struts, a first end of each of the struts connected to one of the attachment structures on one of the fixation plates and a second end of each of the struts connected to one of the attachment structures on another one of the fixation plates, wherein the attachment structures connected to the struts are each connected to two struts.*

*23. The orthopaedic spatial fixation system of claim 15, wherein the struts comprise only six adjustable struts, each strut connected at a first end to one of the attachment structures of one of the fixation plates and each strut connected at a second end to one of the attachment structures of another one of the fixation plates, wherein each attachment structure that is connected to a strut is only connected to one strut.*

*24. The orthopaedic spatial fixation system of claim 15, wherein a chord length between adjacent attachment structures is between about 0.48 inches and about 0.52 inches.*

*25. An orthopaedic spatial fixation system, comprising a plurality of fixation plates wherein each plate comprises a plurality of attachment structures, at least some of the attachment structures being in sets of three attachment points, each plate having a geometrical arrangement defined whereby the three attachment points in a set are spaced substantially 120 degrees apart from each other along an arc of the fixation plate; wherein at least two of the fixation plates are connected to each other by at least six substantially rigid, adjustable length struts, wherein each of the struts are disposed substantially diagonally with respect to its adjacent struts, and the number of attachment structures on each plate being a multiple of 3, whereby rotating the first fixation plate substantially 120 degrees from a starting position in a plane substantially parallel to another one of the fixation plates presents the same geometrical arrangement of attachment points as the geometrical arrangement of attachment points presented to the struts when the first fixation plate is in the starting position.*

*26. The orthopaedic spatial fixation system of claim 25, further comprising an accessory adapted to be attached to one or more of the fixation plates.*

*27. The orthopaedic spatial fixation system of claim 25, wherein the orthopaedic spatial fixation system is adapted to be positioned on a patient.*

*28. The orthopaedic spatial fixation system of claim 25, wherein the struts comprise only six struts, a first end of each of the struts connected to one of the attachment structures on one of the fixation plates and a second end of each of the struts connected to one of the attachment structures on another one of the fixation plates, wherein the attachment structures connected to struts are each connected to two struts.*

*29. The orthopaedic spatial fixation system of claim 25, wherein a chord length between adjacent attachment structures is between about 0.48 inches and about 0.52 inches.*

* * * * *